United States Patent
Brushett

(10) Patent No.: US 12,408,837 B2
(45) Date of Patent: Sep. 9, 2025

(54) RANGE FINDER FOR OCT LUMINAL CLEARANCE

(71) Applicant: CANON U.S.A., INC., Melville, NY (US)

(72) Inventor: Christopher Douglas Brushett, Cambridge, MA (US)

(73) Assignee: Canon U.S.A., Inc., Melville, NY (US)

( * ) Notice: Subject to any disclaimer, the term of this patent is extended or adjusted under 35 U.S.C. 154(b) by 332 days.

(21) Appl. No.: 17/613,258

(22) PCT Filed: Jun. 19, 2020

(86) PCT No.: PCT/US2020/038689
§ 371 (c)(1),
(2) Date: Nov. 22, 2021

(87) PCT Pub. No.: WO2020/257619
PCT Pub. Date: Dec. 24, 2020

(65) Prior Publication Data
US 2022/0218205 A1    Jul. 14, 2022

Related U.S. Application Data

(60) Provisional application No. 62/864,327, filed on Jun. 20, 2019.

(51) Int. Cl.
*A61B 5/00* (2006.01)
*A61B 5/02* (2006.01)
*G01B 9/02091* (2022.01)

(52) U.S. Cl.
CPC .......... *A61B 5/0066* (2013.01); *A61B 5/0084* (2013.01); *A61B 5/02007* (2013.01); *G01B 9/02091* (2013.01)

(58) Field of Classification Search
CPC . A61B 5/0066; A61B 5/0084; A61B 5/02007; A61B 5/7285; G01B 9/02091
See application file for complete search history.

(56) References Cited

U.S. PATENT DOCUMENTS 9,907,536 B2    3/2018    Courtney et al.
2011/0071405 A1    3/2011    Judell et al.
(Continued)

FOREIGN PATENT DOCUMENTS

JP    2014-526283 A    10/2014

OTHER PUBLICATIONS

Rear, R., et al., "Contrast-induced nephropathy following angiography and cardiac interventions", Heart Journal, 2016, pp. 638-648, vol. 102.

(Continued)

Primary Examiner — Ashley K Buran
Assistant Examiner — Dean N Edun
(74) Attorney, Agent, or Firm — Canon U.S.A., Inc., IP Division

(57) ABSTRACT

Disclosed are an apparatus and method for finding a range of lumen clearance, including positioning an imaging probe in a lumen such that the probe tip is positioned to irradiate a target area; acquiring a first set of images of an inside of the lumen while performing a non-flush pullback operation with the probe; analyzing the first set of images to determine a location of the probe tip with respect to a guide catheter; calculating a range of lumen clearance based on the location; and acquiring a second set of images of the inside of the lumen while performing a flush pullback operation only within the calculated range of lumen clearance. Calculating the range of lumen clearance includes calculating a pullback distance from the target area to the distal end of the guide catheter. The method further includes calculating a volume of contrast agent for clearing the calculated pullback distance.

18 Claims, 7 Drawing Sheets

(56) References Cited

U.S. PATENT DOCUMENTS

| | | |
|---|---|---|
| 2011/0190586 A1* | 8/2011 | Kemp .................... A61B 1/12 |
| | | 600/156 |
| 2011/0237958 A1 | 9/2011 | Onimura |
| 2012/0022360 A1 | 1/2012 | Kemp |
| 2012/0101374 A1 | 4/2012 | Tearney et al. |
| 2013/0261441 A1* | 10/2013 | Das ....................... A61B 6/482 |
| | | 600/431 |
| 2013/0310698 A1 | 11/2013 | Judell et al. |
| 2014/0142427 A1 | 5/2014 | Petroff |
| 2014/0180133 A1 | 6/2014 | Brennan et al. |
| 2014/0276016 A1 | 9/2014 | Stigall et al. |
| 2017/0143296 A1* | 5/2017 | Peterson ................ A61B 5/061 |
| 2018/0099125 A1* | 4/2018 | Richer ............ A61M 25/09041 |
| 2019/0059734 A1 | 2/2019 | Yamada |

OTHER PUBLICATIONS

Gutiérrez-Chico, J.L., et al., "A formula to calculate the contrast volume required for optimal imaging quality in optical coherence tomography with non-occlusive technique", Cardiology Journal 2018, 574-581, vol. 25, No. 5.

Buszman, P., et al., "Guiding catheter and guidewire selection for PCT".

Leitgeb, R.A., et al., "Multimodal Optical Medical Imaging Concepts Based on Optical Coherence Tomography", Frontiers in Physics, Oct. 2018, vol. 6, No. 114.

* cited by examiner

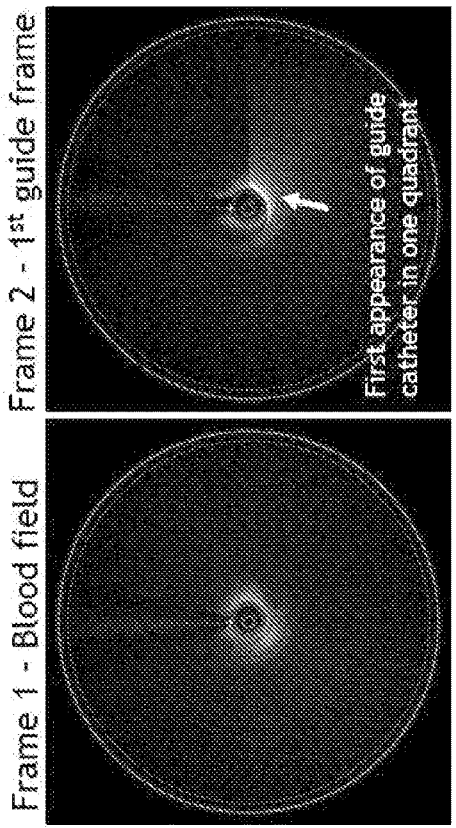

FIG. 5A — Frame 1 - Blood field — Frame indicative of blood field only

FIG. 5B — Frame 2 - 1st guide frame — First appearance of guide catheter in one quadrant — Frame indicative of guide catheter presence FIG. 5C — Frame 3 - Guide tip — Guide catheter tip: Bright surface, homogenous scattering — Frame indicative of guide catheter tip location FIG. 5D — Frame 10 - Guide braided — Guide catheter shaft: Bright surface, dark shadows from braided wires — Frame indicative of guide catheter braided section

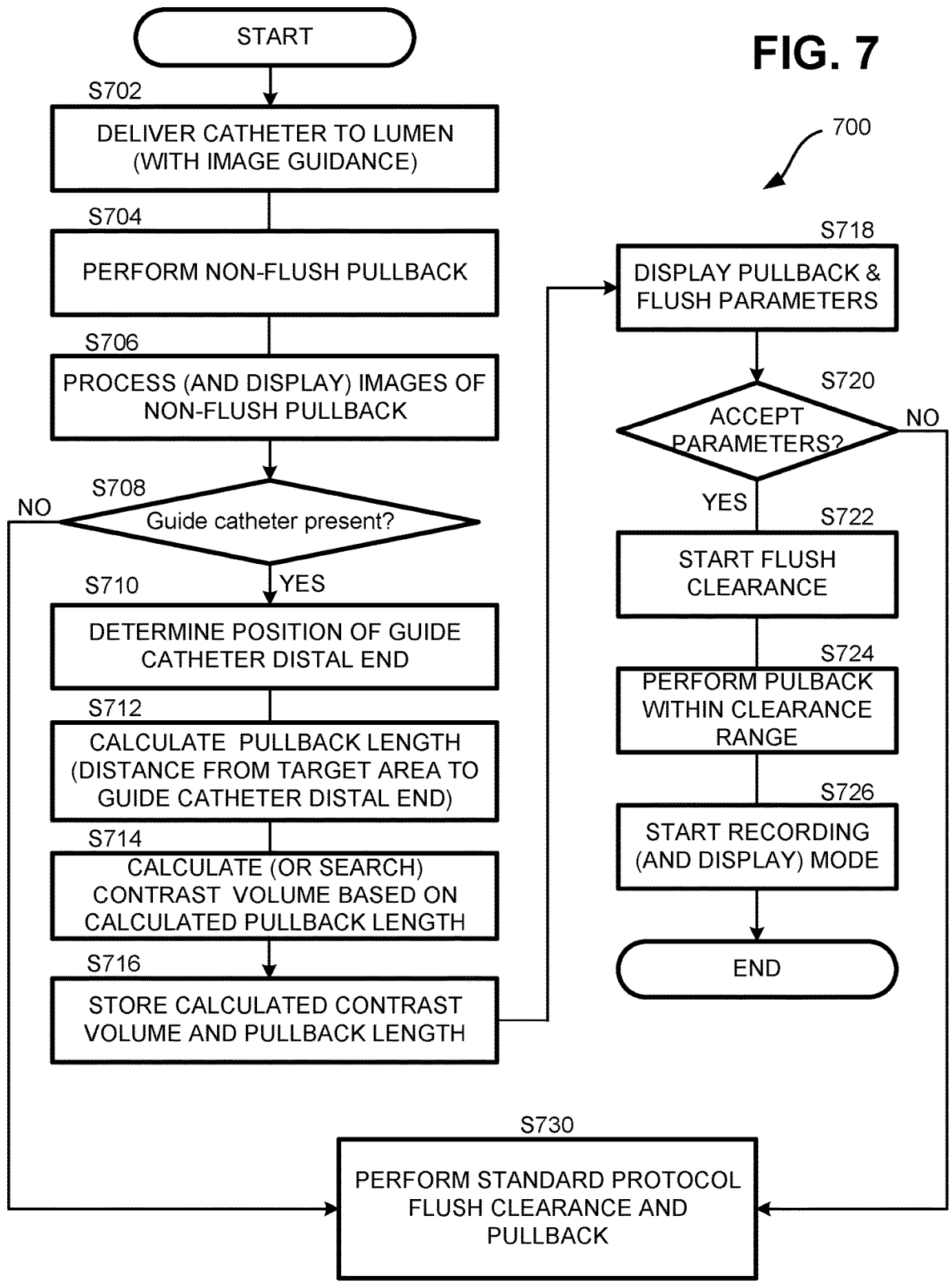

RANGE FINDER FOR OCT LUMINAL CLEARANCE

CROSS-REFERENCE TO RELATED APPLICATIONS

The present application claims priority to U.S. provisional application 62/864,327, filed Jun. 20, 2019, the disclosure of which is incorporated by reference herein in its entirety.

BACKGROUND INFORMATION

Field of Disclosure

The present disclosure generally relates to medical devices. More particularly, the disclosure exemplifies apparatus, methods, and system for performing minimally invasive procedures where an imaging probe requires media displacement (flushing) prior to generating images of a patient's lumen during a pullback operation.

Description of Related Art

Intravascular Optical Coherence Tomography (OCT) requires the infusion of contrast agents to displace blood for clear visualization of the artery wall during imaging. Contrast agents are safe and widely used for displacing blood, but adverse events occur and questions remain about their appropriate use. For example, contrast-induced nephropathy (CIN) is a complication of angiographic procedures and it results from the administration of excessive levels of iodinated and other contrast media. See, e.g., Rear et al., "Contrast-induced nephropathy following angiography and cardiac interventions", Heart Journal, 2016; 102:638-648; doi:10.1136/heartjnl-2014-306962. Therefore, contrast dose is an important factor to be considered for the use of intravascular OCT. Generally, OCT imaging uses a single flush protocol for all pullbacks delivering the same dose of contrast regardless of vessel size, vessel type, or position of the target area. However, target lesions of interest for imaging with OCT may often be located in proximal locations where the full length of pullback and full dose of contrast are not needed. In such cases where target areas are proximal to the imaging catheter, the OCT catheter pulls back into the guide catheter and continues generating images of the guide catheter while unnecessarily continuing to flush the vessel. The foregoing general technique not only wastes considerable amounts of contrast agent, but it also exposes the patient to a risk of contrast-induced side effects.

To address the foregoing issues, there have been certain proposals in technical articles and patent-related publications. For example, Juan Luis Gutierrez-Chico et al., disclosed "A formula to calculate the contrast volume required for optimal imaging quality in optical coherence tomography with non-occlusive technique", published in Cardiology Journal 2018, Vol. 25, No. 5. In this article, the authors report the use of a formula for calculating contrast volume for a flush protocol for OCT imaging based on the length of the Segment of Interest (SOI). The SOI length is estimated using angiography and the dose of flush volume is doubled to account for delays in clearing and triggering at the start of the pullback. The contrast infusion rate is vessel-dependent using the standard infusion rate of 3 milliliter per second [ml/s] for the right coronary artery (RCA) and 4 ml/s for other coronary arteries.

Pre-grant patent application publication US 2011/0237958 A1 discloses and claims an OCT catheter and imaging system, and a technique for detecting in real time whether the imaging catheter has entered the guide catheter. A particular method disclosed in this publication includes detecting the guide catheter directly from raw image data or producing a two dimensional (2D) image and then detecting the guide catheter in the 2D image. This technique includes stopping imaging, stopping the flush operation, or stopping the pullback motors, when the guide catheter is detected from image data. The main drawback of publication US 2011/0237958 A1 is delay time. OCT can be performed at up to 40 mm/s with an entire pullback being performed in 2 seconds or less. Delays in processing the image data, detecting the guide catheter and conveying a stop signal reduces the effectiveness of any potential gains from early stopping. Further, errors in the processing algorithms could cause a premature stop which could ruin an otherwise good pullback and necessitate an additional pullback and additional contrast injection.

U.S. Pat. No. 9,907,536 discloses a multi-modality imaging catheter where one modality is compatible with imaging in blood and the other modality is not. In this patent, IVUS and OCT are respectively used for the two modalities. One specific claim includes using the first, blood compatible, imaging modality to perform a first scan with blood present in the vessel, then analyzing the images to determine if a region of interest is covered by the first scan before performing a second scan with blood displacement using the second modality. Another claim includes using the first modality to perform a first scan with blood present, analyzing the images to identify regions of interest, moving the catheter to a region of interest and then performing a second scan with blood displacement at the new position using the second modality. However, the extra, blood compatible, imaging modality increases the size and cost of the catheter. IVUS pullbacks are very slow compared to OCT, so this method also adds a few minutes to the procedure time.

None of the foregoing related art fully addresses a need to improve contrast flushing techniques. The use of a dual modality, as disclosed by U.S. Pat. No. 9,907,536, increases the size of the device and makes the device more complex and expensive. A main drawback of publication US 2011/0237958 A1 is the potential inaccuracy in timing the stop of infusion and/or pullback during real-time image processing (e.g., either a good pullback could be stopped too early or a poor pullback could be stopped too late). The formula disclosed by Gutierrez-Chico, which relies on angiogram imaging, also suffers of inaccuracies due to the nature of the projection-based imaging modality and the inclusion of estimated delay time. In general, the known techniques result in a larger file sizes, longer image processing time, and greater contrast dose than necessary.

SUMMARY OF EXEMPLARY EMBODIMENTS

The present disclosure provides an apparatus, method and system for determining guide catheter location with respect to a target area (range finding) prior to contrast flushing, and thereby optimizing the image pullback and flushing protocols to avoid excessive contrast dose and reduce processing time.

According to at least one embodiment of the present disclosure, there is provided an apparatus and method for finding a range of lumen clearance for an optical coherence tomographic (OCT) imaging probe, wherein the probe has proximal and distal ends and includes an imaging core and a guiding conduit arranged concentrically to a probe axis, the method comprising: positioning the probe in a lumen such that the distal end of the imaging core is positioned to irradiate a target area; acquiring a first set of images of an inside of the lumen while performing a non-flush pullback operation; analyzing the first set of images to determine a parameter indicative of a position of the imaging core with respect to the guiding conduit; calculating a range of lumen clearance based on the parameter; and acquiring a second set of images of the inside of the lumen only within the range of lumen clearance while performing a flush pullback operation.

In one embodiment, the method of calculating the range of lumen clearance includes calculating a pullback distance from the target area to the distal end of the guiding conduit using the parameter. In one embodiment, the method further includes retrieving, from a pre-stored lookup table, a volume of contrast agent corresponding to the calculated pullback distance. In one embodiment, the method further includes calculating a volume of contrast agent based on the calculated pullback distance.

These and other objects, features, and advantages of the present disclosure will become apparent upon reading the following detailed description of exemplary embodiments of the present disclosure, when taken in conjunction with the appended drawings, and provided claims.

BRIEF DESCRIPTION OF DRAWINGS

Further objects, features and advantages of the present disclosure will become apparent from the following detailed description when taken in conjunction with the accompanying figures showing illustrative embodiments of the present disclosure.

FIGS. 5A, 5B, 5C, 5D illustrate a plurality of exemplary reconstructed OCT axial images (OCT frames) acquired during a non-flush pullback operation.

FIG. 7 illustrates a first exemplary range finding algorithm for controlling the OCT system 100 to perform luminal clearance according to a first embodiment.

DETAILED DESCRIPTION OF EXEMPLARY EMBODIMENTS

Figure 1:
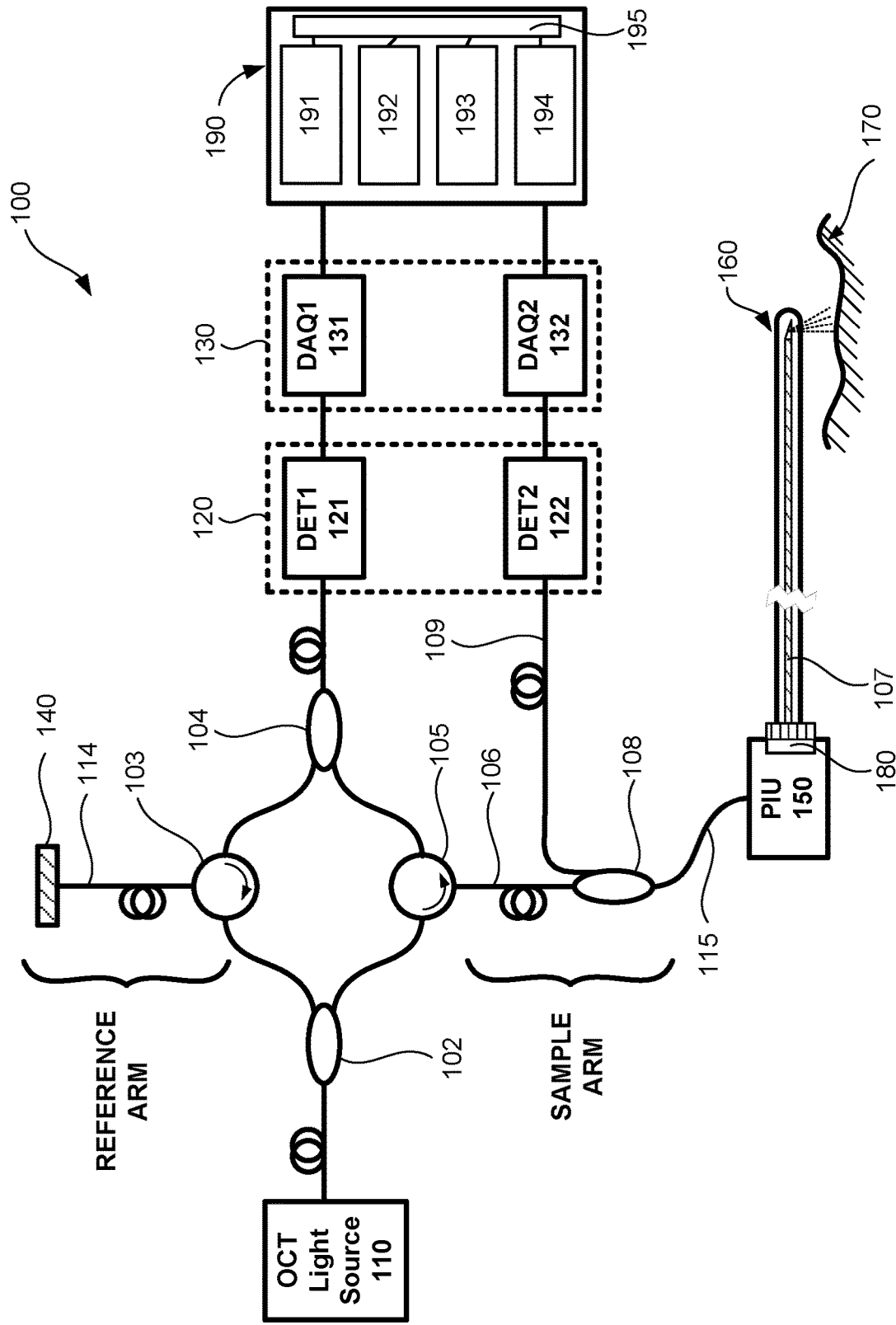
FIG. 1 is a diagram of an exemplary OCT system 100 having a range finder for OCT luminal clearance according to an embodiment of the present disclosure.

The embodiments are based on the object of providing an apparatus, method and system for determining guide catheter position prior to contrast flushing and optimizing the imaging pullback distance and flushing protocol to avoid wasted contrast dose.

Throughout the figures, the same reference numerals and characters, unless otherwise stated, are used to denote like features, elements, components or portions of the illustrated embodiments. In addition, while the subject disclosure is described in detail with reference to the enclosed figures, it is done so in connection with illustrative exemplary embodiments. It is intended that changes and modifications can be made to the described exemplary embodiments without departing from the true scope and spirit of the subject disclosure as defined by the appended claims. Although the drawings represent some possible configurations and approaches, the drawings are not necessarily to scale and certain features may be exaggerated, removed, or partially sectioned to better illustrate and explain certain aspects of the present disclosure. The descriptions set forth herein are not intended to be exhaustive or otherwise limit or restrict the claims to the precise forms and configurations shown in the drawings and disclosed in the following detailed description.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached", "coupled" or the like to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown in one embodiment can apply to other embodiments. It will also be appreciated by those of skill in the art that references to a structure or feature that is disposed "adjacent" to another feature may have portions that overlap or underlie the adjacent feature.

In referring to the description, specific details are set forth in order to provide a thorough understanding of the embodiments disclosed. Some aspects of the present disclosure may be implemented by a computer system that includes, in general, one or a plurality of processors for processing data including instructions, random access (volatile) memory (RAM) for storing data and instructions or programs, read-only (non-volatile) memory (ROM) for storing static information and instructions, a data storage devices such as a magnetic or optical disk and disk drive for storing information and instructions, an optional user output device such as a display device (e.g., a LCD or OLED monitor) for displaying information to a user, an optional user input device including alphanumeric and function keys (e.g., a keyboard or touchscreen) for communicating information and command selections to the processor, and an optional user input device such as a pointing device (e.g., a mouse) for communicating user input information and command selections to the processor.

In the present application, the described embodiments may be implemented as an apparatus, a method, or non-transitory computer-readable medium product storing thereon one or more programs. Accordingly, some implementations may take the form of an entirely hardware embodiment, an entirely software embodiment (including firmware, resident software, micro-code, etc.), or an embodiment combining software and hardware aspects that may all generally be referred herein as a "module", a "unit", or a "system". Some embodiments described below with reference to flowchart illustrations and/or block diagrams may be implemented by computer-executable programed instructions. The computer program instructions may be stored in computer-readable media that when executed by a computer or other programmable data processing apparatus causes the computer or processing apparatus or processor to function in a particular manner, such that the instructions stored in the computer-readable media constitute an article of manufacture including instructions and processes which implement the function/act/step specified in the flowchart and/or block diagram.

The terms first, second, third, etc. may be used herein to describe various elements, components, regions, parts and/or sections. It should be understood that these elements, components, regions, parts and/or sections are not limited by these terms of designation. These terms of designation have been used only to distinguish one element, component, region, part, or section from another region, part, or section. Thus, a first element, component, region, part, or section discussed below could be termed a second element, component, region, part, or section merely for purposes of distinction but without limitation and without departing from structural or functional meaning.

As used herein, the singular forms "a", "an", and "the" are intended to include the plural forms as well, unless the context clearly indicates otherwise. It should be further understood that the terms "includes" and/or "including", "comprises" and/or "comprising", "consists" and/or "consisting" when used in the present specification and claims, specify the presence of stated features, integers, steps, operations, elements, and/or components, but do not preclude the presence or addition of one or more other features, integers, steps, operations, elements, components, and/or groups thereof not explicitly stated. Further, in the present disclosure, the transitional phrase "consisting of" excludes any element, step, or component not specified in the claim. It is further noted that some claims may be drafted to exclude any optional element; such claims may use exclusive terminology as "solely," "only" and the like in connection with the recitation of claim elements, or it may use of a "negative" limitation.

The present disclosure generally relates to medical devices, and it exemplifies embodiments of a probe of an optical coherence tomographic (OCT) apparatus. The embodiments of the OCT probe and portions thereof are described in terms of their state in a three-dimensional space. As used herein, the term "position" refers to the location of an object or a portion of an object in a three-dimensional space (e.g., three degrees of translational freedom along Cartesian X, Y, Z coordinates); the term "orientation" refers to the rotational placement of an object or a portion of an object (three degrees of rotational freedom—e.g., roll, pitch, and yaw); the term "posture" refers to the position of an object or a portion of an object in at least one degree of translational freedom and to the orientation of that object or portion of the object in at least one degree of rotational freedom (up to six total degrees of freedom); the term "shape" refers to a set of posture, positions, and/or orientations measured along the elongated body of the object. As it is known in the field of medical devices, the terms "proximal" and "distal" are used with reference to the manipulation of an end of an instrument extending from the user to a surgical or diagnostic site. In this regard, the term "proximal" refers to the portion of the instrument closer to the user, and the term "distal" refers to the portion of the instrument further away from the user and closer to the surgical or diagnostic site.

As used herein the term "catheter" generally refers to a flexible and thin tubular instrument made of medical grade material designed to be inserted through a narrow opening into a bodily lumen (e.g., a vessel) to perform a broad range of medical functions. The more specific term "optical catheter" refers to a medical instrument comprising an elongated bundle of one or more flexible light conducting fibers disposed inside a protective sheath made of medical grade material and having an optical imaging function.

A guide catheter is a special type of hollow catheter that provides a conduit for the passage of interventional equipment and delivery for contrast media to a target site. Guide catheters are made up of three layers including an inner polytetrafluoroethylene layer that is slippery, a middle stainless steel braided layer, and an outer soft nylon elastomer jacket. The inner layer has a lubricious coating and facilitates easy passage of the catheter; the middle stainless steel braided layer stiffens the catheter to provide support for passage of the device; the outer coating provides flexibility. The internal diameter of a guide catheter facilitates delivery of equipment and injection of contrast. Guide catheters have differential stiffness throughout; the proximal part is the stiffest and gradually softens towards the distal tip. Guide catheters are typically sized based on the outer diameter (French size). A 7-Fr guide catheter fits through a 7-Fr sheath, but a 7-Fr device does not fit through a 7-Fr guiding catheter. Guiding catheters are available with various tip configurations, and some may include radiopaque marker bands for identification purposes.

In the present disclosure, the terms "optical fiber", "fiber optic", or simply "fiber" refers to an elongated, flexible, light conducting conduit capable of conducting light from one end to another due to the effect known as total internal reflection. The term "fiber" may refer to one or more light conducting fibers. A fiber has a transparent, homogenous core, where the light is guided, and the core is surrounded by a homogenous cladding. The refraction index of the core is larger than the refraction index of the cladding. Depending on design choice some fibers can have multiple claddings surrounding the core.

In the present disclosure, prior to performing any standard OCT pullback procedure in vivo with contrast flush, we perform a first pullback without flush (a non-flush pullback). That pullback will not produce any clear images of the vessel due to the presence of blood, but the guide catheter will be identifiable (if present). The system can use the non-flush pullback to determine the guide catheter position either manually or automatically with a software algorithm, and then measure the length from the guide catheter tip to the imaging start position (e.g., an area of interest) which gives the available pullback length in the vessel. From the foregoing, the system can calculate an optimal volume of contrast agent for flushing the vessel based on the available pullback length, and then perform a second OCT pullback using the calculated optimal volume of contrast agent for flushing the vessel.

<OCT Imaging System>

FIG. 1 illustrates a general structure of an exemplary system 100 including an interferometric OCT modality that can be applied as an intravascular OCT system for imaging of coronary arteries or other bodily lumens. For example, the system 100 may also be adapted to be used for esophageal imaging. As depicted in FIG. 1, the system 100 includes an OCT modality comprised of an interferometer, a computer 190 and an imaging probe 160. The interferometer includes a sample arm and a reference arm, a light source 110, a detector unit 120, and data acquisition electronics 130 connected to the computer 190. The sample arm includes a patient interface unit (PIU) 150 and the imaging probe 160 which is connected to the PIU 150 via a catheter connector 180. In one embodiment, the system 100 may use a swept-source laser (wavelength 1310 nm+/−50 nm) as the OCT light source 110. The imaging probe 160 (also referred to as "catheter 160") includes one or more optical fibers extending from the proximal end to the distal end of the imaging probe. The basic function of the OCT imaging probe is to deliver and focus an imaging beam onto a sample 170, scan the beam on the sample, collect the back-reflected light from the sample, and transmit the collected light back to the OCT interferometer. In one embodiment, the imaging probe 160 may include double clad fiber (DCF) with a polished ball lens at the tip thereof for side-view imaging. The imaging probe may alternatively include a DCF, a GRIN lens, and a refractive element (e.g., a grating) for forward-view imaging.

Light (radiation) from the light source 110 is guided through the sample arm to a target area sample 170; the same light from light source 110 is also guided through the reference arm to a reflector 140. Light returning from the sample and reference arms generate OCT interference patterns in a known manner. Specifically, light from the light source 110 is split by a splitter 102 (fiber splitter or beam splitter) into a sample beam and a reference beam which are respectively conveyed to the sample arm and the reference arm via respective optical fibers. In the sample arm, the sample beam enters a circulator 105, passes to a fiber coupler 108 via a single-mode (SM) fiber 106, and the sample beam is delivered to the catheter 160 via a double clad fiber 107. The catheter 160 is connected at the proximal end thereof to the PIU 160; and the PIU 160 is in turn connected to computer 190. Under control of the computer 190, the PIU 160 controls the sample beam to irradiate the sample 170 in a scanning manner. Light of the sample beam reflected and/or scattered by the sample 170 is collected by optics (an optical probe) arranged at the distal end of the catheter 160; and the collected light is transmitted back through the double clad fiber 107 to the PIU 150 and to fiber coupler 108. The fiber coupler 108 transmits one part of the sample beam towards the circulator 105 via the SM fiber 106; in turn, the circulator 105 guides the one part of the sample beam to the combiner 104. In addition, the fiber coupler 108 couples another part of the sample beam to a second detector 122 via a fiber 109.

In the reference arm, light of the reference beam enters a circulator 103 and is delivered to the reflector 140 via an optical fiber 114. In the case of Time Domain OCT (TD-OCT), the reflector 140 may be implemented as a scanning mirror. And, in the case of Frequency Domain OCT (FD-OCT), the reflector 140 may be implemented as a stationary mirror. Light of the reference beam reflected from the reflector 140 passes through the circulator 103, and is also guided to the combiner 104. In this manner, the sample and reference beams are combined at the beam combiner 104 and then detected by detector 121 to generate interference signals according to known OCT principles.

The output of the interferometer (interference patterns) is detected by the detector 121 of the detection unit 120. The first detector 121 may be implemented as an array of photodiodes, a photo multiplier tube (PMT), a multi-array of cameras or other similar interference pattern detecting device. The signals output from the first detector 121 are pre-processed by data acquisition electronics (DAQ1) 131, and transferred to computer 190. The computer 190 performs signal processing to generate OCT images in a known manner. The interference patterns are generated only when the path length of the sample arm matches the path length of the reference arm to within the coherence length of light source 110.

The second detector 122 detects a part of the sample beam transmitted from the fiber coupler 108 via the fiber 109. The second detector 122 outputs an analog signal corresponding to an intensity of the backscattered light (backscattered signal). The signal output from detector 122 is converted to digital data with data acquisition electronics (DAQ2) 132. The intensity of the OCT backscattered light may be used as a trigger signal for starting and/or ending pullback and image recording operations. Therefore, the signal output from detector 122, and converted to digital data by data acquisition electronics (DAQ2) 132 can be used directly as a trigger signal or it can be transferred to the computer 190 for control processing. U.S. patent application Ser. No. 15/68,951, published as US 2019/0059734 A1 and assigned to the assignee of the present application, discloses a fiber optic imaging apparatus that uses a cladding mode of the fiber for triggering lumen clearance, and control methods therefor. U.S. patent application Ser. No. 15/68,951 is incorporated by reference herein in its entirety.

Computer 190 includes a central processing unit (CPU) 191, a storage memory (ROM/RAM) 192, a user input/output (I/O) interface 193, and a system interface 194. The various components of the computer 190 communicate with each other via a data bus (BUS) 195 in a known manner.

Storage memory 192 includes one or more computer-readable and/or writable media, and may include, for example, a magnetic disc (e.g., a hard disk drive HHD), an optical disc (e.g., a DVD®, a Blu-ray®, or the line), a magneto-optical disk, semiconductor memory (e.g., a non-volatile memory card, Flash® memory, a solid state drive, SRAM, DRAM), an EPROM, an EEPROM, etc. Storage memory 192 may store computer-readable data and/or computer-executable instructions including Operating System (OS) programs, and control and processing programs.

The user interface 193 provides a communication interface (electronic connections) to input/output (I/O) devices, which may include a keyboard, a display (LCD or CRT), a mouse, a printing device, a touch screen, a light pen, an external optical storage device, a scanner, a microphone, a camera, a drive, communication cable and a network (either wired or wireless).

The system interface 194 also provides communication interfaces (electronic connections) for one or more of the light source 110, detectors 121-122, data acquisition electronics DAQ1 (131) and DAQ2 (132), and the patient unit interface (PIU) 150. The system interface 194 may include programmable logic for use with a programmable logic device (PDL), such as a Field Programmable Gate Array (FPGA) or other PLD, discrete components, integrated circuitry (e.g., an Application Specific Integrated Circuit (ASIC)), or any other components including any combination thereof.

The function of the user interface 193 and of the system interface 194 may be realized at least in part by computer executable instructions (e.g., one or more programs) recorded in storage 192. Moreover, the computer 190 may comprise one or more additional devices, for example, components such as a communications or network interface, a circuit interface (e.g., a field-programmable gate array:

FPGA) to control one or more of the light source 110, detectors 121-122, mirror 140, and PIU 150.

The CPU 191 is comprised of one or more processors (e.g., a microprocessor, microcontroller, digital signal processor) configured to read and execute computer-executable instructions stored in the storage memory 192. The computer-executable instructions may include executable code for the performance of the novel processes, methods and/or calculations disclosed herein. For example, CPU 191 calculates the intensity backscattered light based on electric signals output from optical detectors (121-122) and preprocessed by the acquisition electronics 130, and using the OCT signals, CPU 191 can calculate the catheter pullback distance (axial movement) and the dose or volume of flushing agent required, as explained more in detail in the remaining detailed description.

<Optical Probe>

Figure 2:
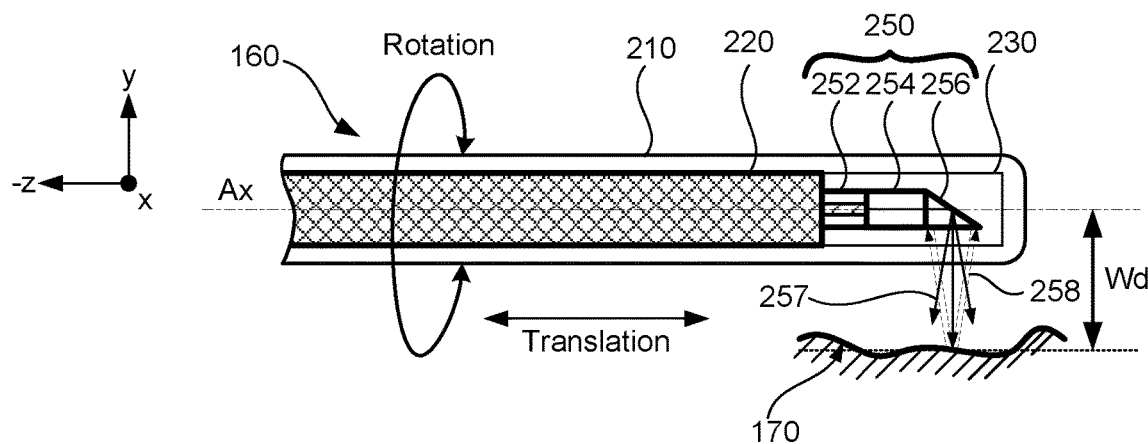
FIG. 2 illustrates an exemplary representation of a distal end of catheter 160 (an optical probe) of the OCT imaging system 100.

FIG. 2 illustrates an exemplary representation of a distal end of catheter 160 (an optical probe). As illustrated in FIG. 2, catheter 160 comprises an outer sheath 210, a coil 220, a transparent protector 230, and an optical probe 250. The optical probe 250 includes a double clad fiber (DCF) 252, a lens 254 (e.g., a GRIN lens), and a reflecting or diffracting surface 256. The catheter 160 is connected at the proximal end thereof to the PIU 150 via the catheter connector 180 (as shown in FIG. 1). The coil 220 delivers rotational torque from the proximal end to the distal end of catheter 160. The rotational torque is provided by one or more motors located in the PIU 150. At the distal end of the probe 250, the reflecting surface or diffracting surface 256 (e.g., a mirror, a prism, or a grating) directs illumination light (sample beam) toward the target area of sample 170 (e.g., the wall of a lumen cavity). As shown in FIG. 2, the probe 250 is configured for side-view imaging, where the illumination light 257 incident on the target area travels at a transverse angle with respect to the catheter's axis Ax. Here, illumination light refers to light originated from OCT light source 110.

The optical probe is fixed to coil 220 so that a distal tip (distal end) of the optical probe also spins (rotates or oscillates with respect to the axis Ax) to obtain an omnidirectional view of the inner surface of hollow organs, such as vessels of a subject (patient). At the proximal end of the optical probe 250 the double clad fiber 252 is connected with the PIU 150 via a non-illustrated fiber connector. The double clad fiber 252 is used to deliver illumination light 257 through its core, and to collect backscattered light 258 from the sample 170 through the core and/or cladding. The lens 254 is used for focusing and collecting light to and/or from the sample 170, which is located at a working distance (Wd) from the catheter 160. The intensity of backscattered light transmitted through the cladding of fiber 252 is typically higher than the intensity of backscattered light collected through the core because the size of the core is much smaller than the cladding.

<Fiber Optic Rotary Joint>

Figure 3:
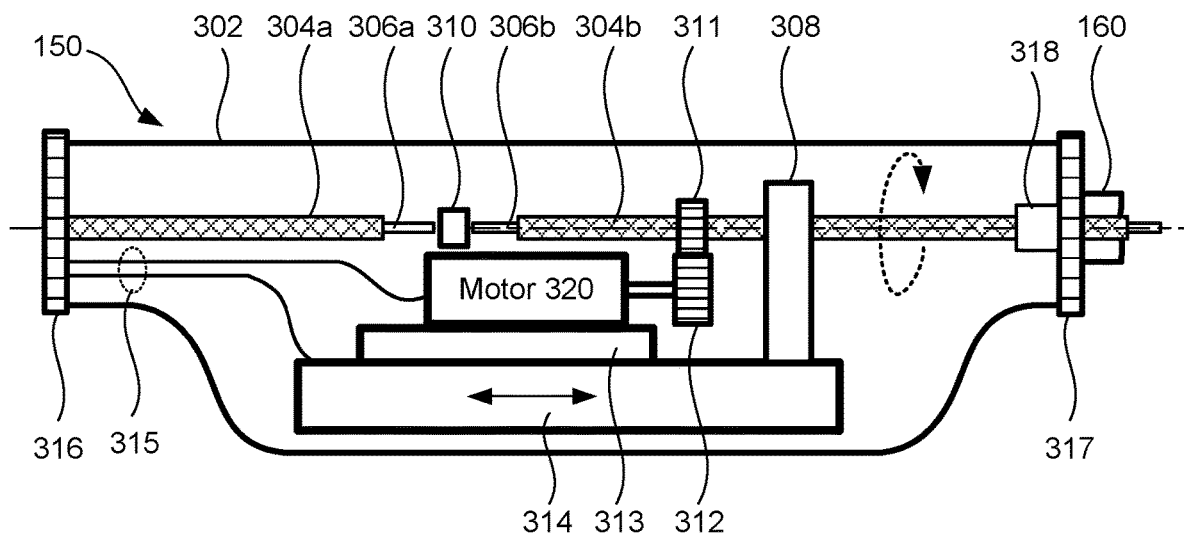
FIG. 3 schematically shows one exemplary implementation of a patient interface unit (PIU) 150 housing is a fiber optic rotary joint (FORJ) of the OCT imaging system 100.

FIG. 3 schematically shows one exemplary implementation of relevant parts of a patient interface unit (PIU) 150 which is located at the proximal end of the catheter 160 (as shown in FIG. 1). As shown in FIG. 3, the PIU 150 is encased in an outer housing 302, which serves as a housing for mechanical, electronic, and optical components useful for control of the optical probe and catheter. Also included in the housing 302 is a fiber optic rotary joint (FORJ) comprised of a rotational motor 320, a motorized translation stage 314, and free-space optical connections 310. At one end, the PIU 150 is provided with an optical/electrical connector 316, and at the other end thereof the PIU 150 is provided with an optical connector 318 (e.g., a fiber connector), which engages with the fiber of the catheter 160. A mechanical connection 317 serves to mechanically engage (connect) the PIU 150 to the catheter 160. A double clad fiber 306*a* encased in a sheath 304*a* and electronic wiring connections 315 connect the PIU 150 to the computer 190 via the connector 316. A double clad fiber 306*b* encased in a sheath 304*b* engages (connects) with catheter 160, when the catheter 160 is connected to the PIU 150 via the catheter connector 317. It is understood that other elements such as a guidewire and one or more conduits, e.g., for delivering a blood clearing medium (liquid), can be included in the catheter 160. In addition, although a single DCF 306*a* and a single DCF 306*b* are shown, more than one fiber can be used to transmit the light from OCT light source 110.

The motor 320 and motorized translation stage 314 provide rotational and translational torque for actuation of the movable components of catheter 160. Motor 320, for example, drives a non-labeled shaft to rotate a gear 312 which transfers rotational torque to a gear 311. The motor 320 is mechanically fixed to a base plate 313. In addition, a motorized translation stage 314 is also fixed to the base plate 313. The motorized translation stage 314 serves to provide translational torque for controlling linear movement (insertion into a lumen or pullback) of the movable components within catheter 160. A support 308 provides support and directional control for translational movement of the movable components within catheter 160. In other words, support 308 serves as a linear guide for translational movement. The motorized translation stage 314 is also used for providing translational torque during pullback. The connector 317 is a catheter connector which mechanically engages with the proximal end of the catheter, and the connector 318 aligns and connects the rotating parts of the FORJ with the rotating parts of catheter 160.

Rotational and translational torque for actuation of the movable components of catheter 160 is not limited to motorized movement. Instead of motors and mechanical gears, rotational and translational torque may also be implemented by using pneumatic or electromagnetic driving mechanisms to achieve rotary and forward/backward mechanical movement. See, for example, publication US 20140180133 (Brennan et al.), which is incorporated by reference herein in its entirety. In addition, ultrasonic motor (USM) systems may be advantageously used, for example, in a case where the imaging probe is intended to be used under the magnetic field of an MR-based modality. USM or pneumatic drive mechanisms can be used in the FORJ to avoid the effects that a magnetic field would have on metallic based driving mechanisms.

<Pullback Operation>

Figure 4A:
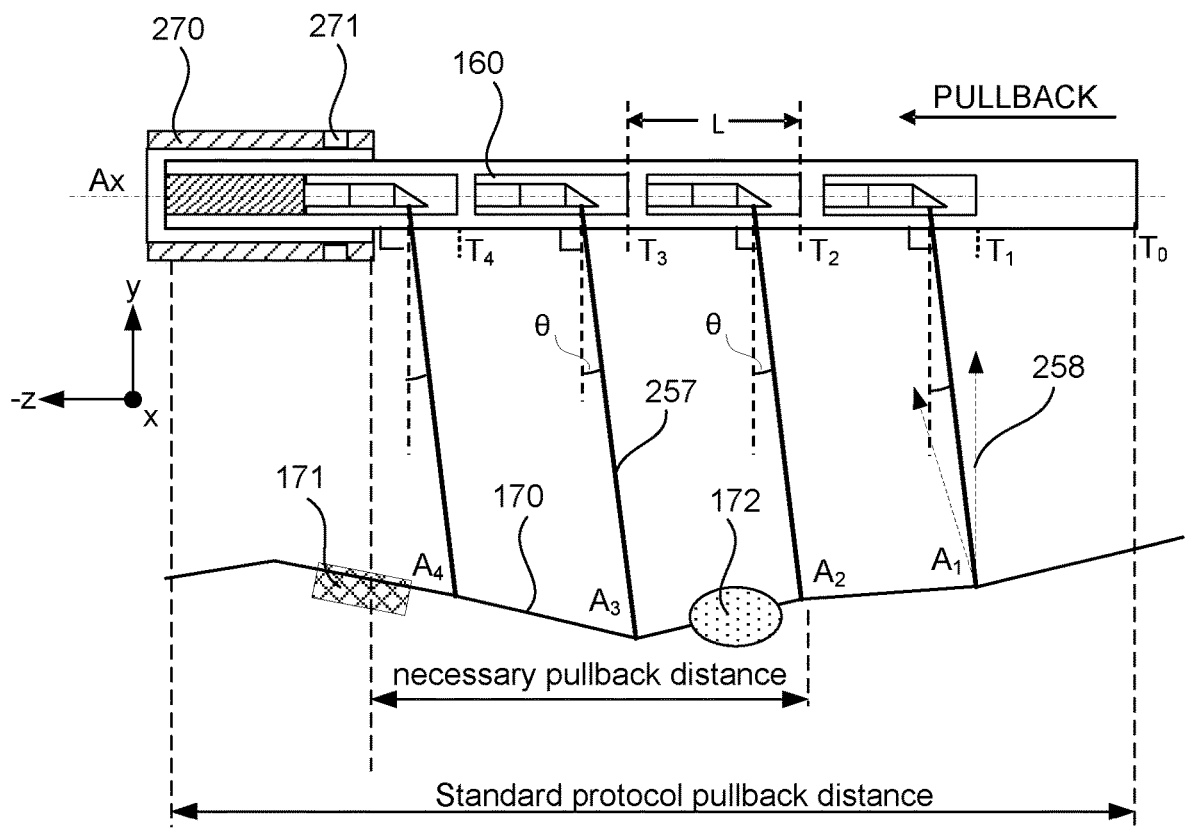
FIG. 4A and FIG. 4B respectively illustrate a transverse view and an axial view of the distal end (optical probe) of the catheter 160 at sequential positions during a pullback operation.

FIG. 4A illustrates a transverse view of the distal end (optical probe) of the catheter 160 at sequential positions during a pullback operation. As shown in FIG. 4A, during a pullback operation, the catheter 160 is simultaneously rotated (moved around its axis) and translated (moved linearly) inside a guide catheter 270. The guide catheter 270 includes one or more ports 271 for delivering flushing media or contrast agent, such as saline solution or the like. As known to those of ordinary skill in the art, intra-luminal OCT uses a helical scan to form a plurality A-line scans (A1, A2, A3, A4) obtained at a predetermined distance L depending on a scan rate of the OCT system. The diagram of FIG. 4A depicts a plurality of positions (a plurality of locations T1, T2, T3, T4 along the longitudinal direction) of the catheter 160 at corresponding timings t1, t2, t3, t4, along the pullback path, where the OCT system 100 acquires a corresponding plurality of two-dimensional images of lumen sample 170. To that end, the optical probe 252 inside of catheter 160 scans the inner surface of the sample 170, a target area 172, and possibly a known reference 171, by projecting an illumination beam of light 257 at a transverse angle θ and collecting backscattered light 258.

In the transverse view shown in FIG. 4A, the transverse angle θ of illumination light 257 projected on the sample 170 can be fixed or it can be adjustable (e.g., to compensate for non-uniform rotational distortion). For simplicity, in the present disclosure, transverse angle θ is assumed to be fixed.

Figure 4B:
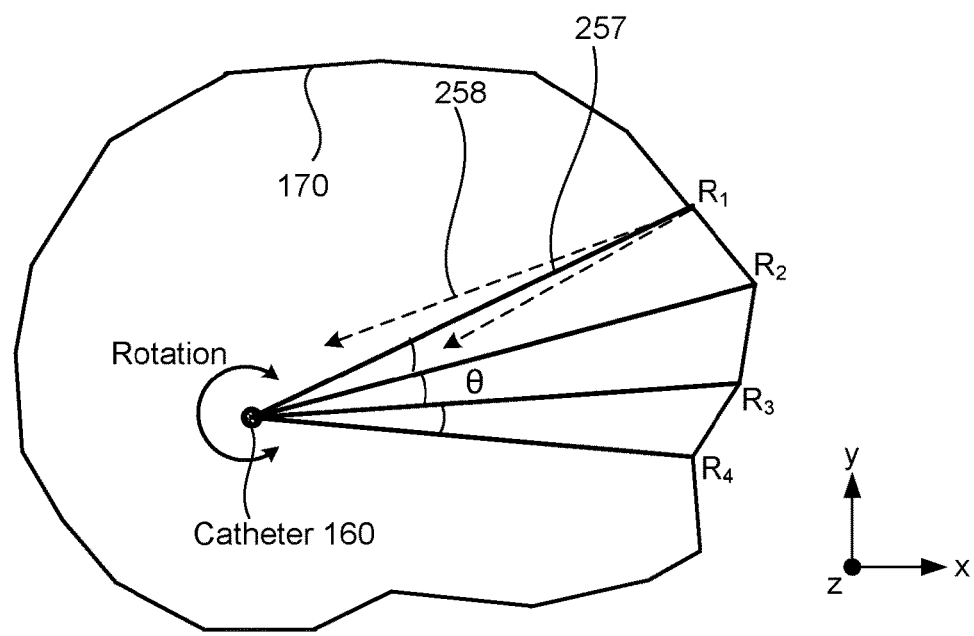

FIG. 4B illustrates an axial view of the distal end of catheter 160 with exemplary illumination light 257 incident on sample 170 (e.g., a blood vessel wall) at a plurality of radial locations R1, R2, R3, R4 along a helical path. Measurements at each location are performed, by collecting backscattered light 258 from each location, while scanning the sample 170 with a fixed (same) axial angle θ. Each of locations R1, R2, R3, and R4 represents a different location (a different point) on the sample surface at which a measurement is made while the optical probe of catheter 160 rotates and translates linearly.

As illustrated in FIGS. 4A-4B, in a three dimensional (3D) space defined by x, y, z Cartesian coordinates, the minus z direction (−z) represents the pullback direction of catheter 160, and the point where the 3 axes converge represents a point source (point light source) from which illumination light 257 is projected onto the sample 170 and/or at which the backscattered light 258 is collected from the sample 170. From this point source, during a pullback operation, light is projected along the x-y plane (in the axial direction) while the probe rotates, and along the z-y plane while the probe moves linearly (in the transversal direction). Accordingly, in the 3D environment, a plurality of 2D images (or frames) can be reconstructed by combining the plurality of lines scans A1, A2, A2, A4, at corresponding times t1-t4 respectively, while the probe rotates and scans the inner wall of sample 170, using the projections of the illumination light 257 and collection of backscattered light 258 in both the transversal plane and the axial plane.

As explained above, a pullback operation (shown in FIG. 4A) is typically performed according to a standard protocol where the entire pullback distance traveled by the catheter 160 may not take into account the actual position of a target area 172 or the actual position of the distal end of the guide catheter 270. In that case, the amount of contrast agent and the time for performing the pullback are not optimized. As noted above, it is well known in the field of medicine that contrast agents can have some deleterious effects on patients, but it is also known that inadequate displacement of blood results in sub-optimal imaging. Therefore, the present disclosure provides herein a novel technique to first perform a non-flush pullback according to standard protocol, detect and locate the distal end of the guide catheter, and then calculate a reduced volume of contrast agent based on the actual and/or necessary pullback distance.

Guide catheters typically consist of a long shaft braided with metal wire and a short one to two millimeters (1-2 mm) soft, unbraided, and atraumatic tip. Guide catheters usually have a stiff metallic body and a soft floppy tip to enable easy tip navigation. The guide catheter serves as a guiding conduit for delivering the imaging probe (catheter 160) to an area of interest inside an intraluminal cavity, e.g., a vessel. A guide catheter may comprise a 6 Fr to 8 Fr guide catheter, or a 5 Fr to 6 Fr intermediate catheter, or even smaller ones known as microcatheters.

Under OCT imaging, a guide catheter can be identified by analyzing a set images acquired in an OCT pullback operation even without blood clearance by its characteristic appearance. FIGS. 5A-5D illustrate a plurality of exemplary reconstructed axial images (frames) acquired during a non-flush pullback operation. In the reconstructed OCT images of FIGS. 5A-5D, the soft tip of the guide catheter 270 first appears as a bright ring of constant diameter with homogeneous scattering (see, e.g., FIGS. 5A, 5B and 5C). The soft tip of the guide catheter scatters light differently than blood does, so there is an increase in signal intensity away from the catheter outer surface, as the image transitions from imaging blood into imaging the tip of the guide catheter. Pulling back the catheter further into the guide catheter, the metal braids of the guide catheter create shadows giving the guide catheter a distinct appearance like sun rays (see FIG. 5D). Therefore, according to at least one embodiment of the present disclosure, the inventor(s) herein have disclosed specialized software algorithms that can, among other features, automatically detect both the braided and soft tip sections of the guide catheter from OCT images with high accuracy and minimal processing time. Once the guide catheter has been identified, the software takes over and does the pullback length and contrast volume calculations. The software may then prompt the user to accept the calculated settings which can then be set automatically or displayed for the user to set.

FIG. 5A shows a first frame (Frame 1) of the Blood field. More specifically, Frame 1 shows a blood field image, an image taken at positions T1 or T2 in FIG. 4A, where only the blood field can be imaged. FIG. 5B shows a second frame (Frame 2) in which the distal end of the guide catheter 270 first appears. FIG. 5C shows a third frame (Frame 3) where the guide catheter tip forms a bright (almost full) circle due to homogenous scattering from the guide catheter tip. Finally, FIG. 5D shows a later frame (e.g., Frame 10) where the braided shaft of the guide catheter 270 is clearly visible from the sun-like rays shown in this image. The frame shown in FIG. 5D is indicative that the optical probe of catheter 160 has been fully pulled-back into the lumen of the guide catheter 270. However, to optimize the pullback time and minimize the dose of flushing media, it is advantageous to precisely detect the distal end (tip) of the guide catheter before the catheter 160 is pulled back into the lumen of the guide catheter 270.

Figure 6A:
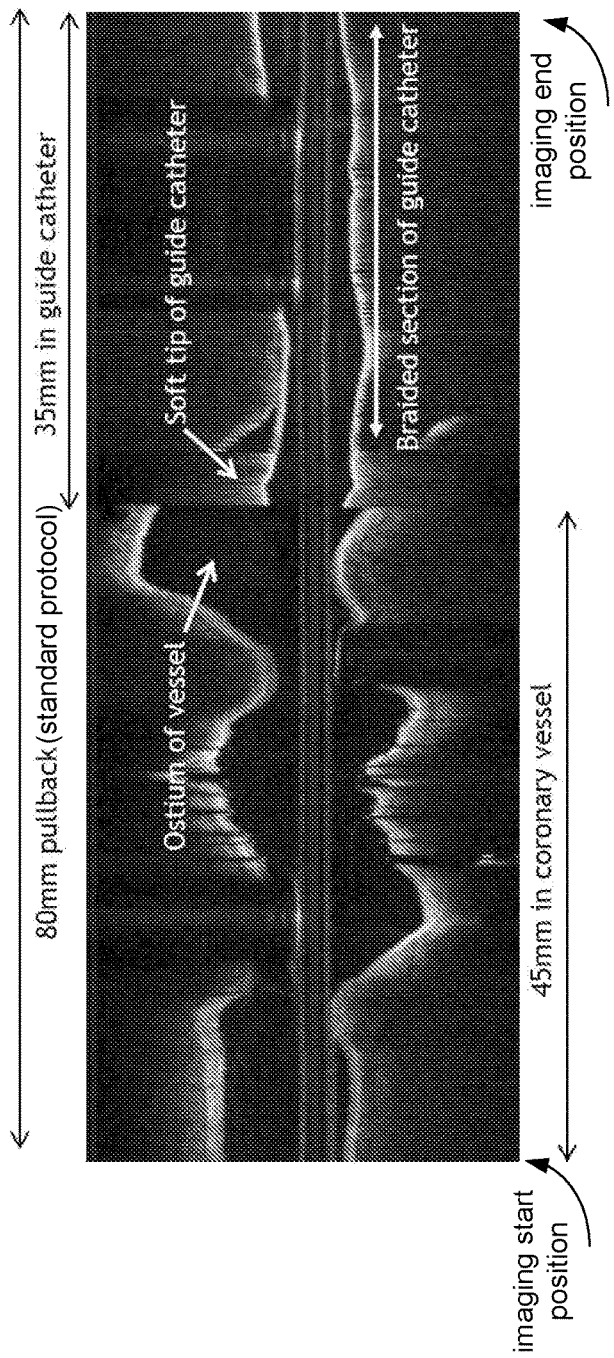
FIG. 6A illustrates an exemplary reconstructed OCT image with corresponding pullback parameters.
Figure 6B:
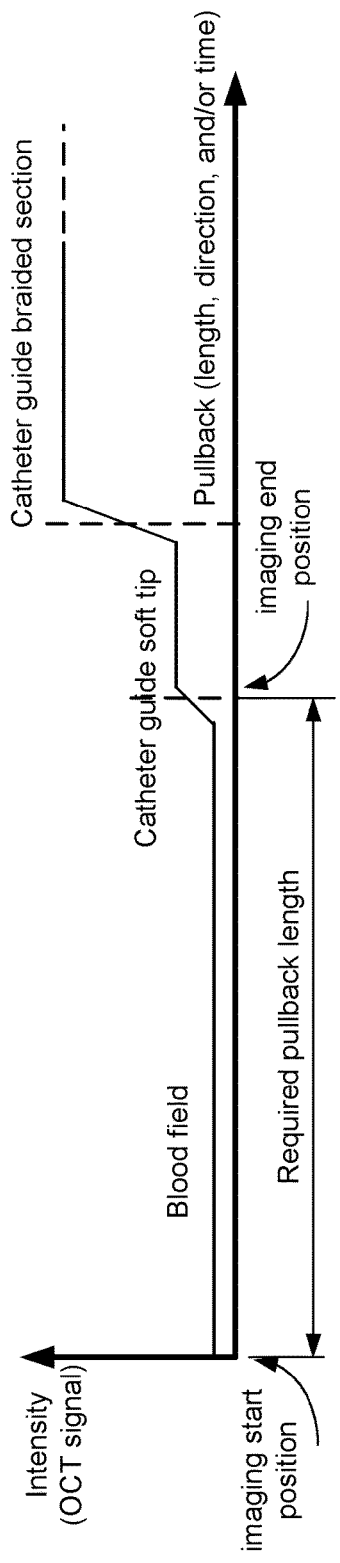
FIG. 6B illustrates an exemplary graph of brightness levels as a function of pullback parameters.

Alternatively or in addition, the guide catheter can be identified by analyzing an intensity signal detected during an OCT pullback operation even without blood clearance. FIG. 6A shows an exemplary reconstructed OCT image of a typical pullback operation (a pullback operation according to a standard protocol). In FIG. 6A, the imaging start position and imaging end position are based on a standard flush protocol with a pullback length of about 80 mm. However, as shown in FIG. 6B, it is possible to optimize the pullback length, by detecting and distinguishing the changes in intensity signal corresponding to light scattered by the blood field, the catheter guide soft tip, and the catheter guide braided section. Specifically, under a non-flush pullback operation, the blood field initially generates an OCT signal of low intensity due to the scattering properties of blood. As the catheter is pulled back into the catheter guide soft tip, the OCT intensity signal increases (e.g. as shown in FIGS. 5B and 5C). Moreover, as the catheter is further pulled inside the braided section of the catheter tip, the intensity of the OCT signal becomes substantially higher (e.g., as shown in FIG. 5D). Therefore, the presence and/or location of the guide catheter 270 can be used to first calculate the minimum required pullback length.

FIG. 7 illustrates an exemplary flow process for controlling the OCT system to perform guide catheter tip detection and calculation of effective (necessary) pullback distance, as well as calculation of a reduced dose of contrast agent for flushing during OCT imaging. The process of FIG. 7 assumes an operational state in which a non-illustrated system console including computer 190 undergoes a system setup. System console setup may include, for example, executing a booting sequence of computer 190 and initializing the system software that operates the OCT system 100. In addition, system setup may include, the computer 190 accessing executable software code stored in data storage memory 192 and initiating an imaging operation upon receiving a command prompt from a user of the system.

<Range Finding Algorithms for OCT Luminal Clearance>

In one embodiment an OCT pullback may be performed without injection of contrast agent and displayed in a standard view. This non-flush pullback can be performed using standard pullback protocols. The user could be prompted to find the guide catheter by analyzing the OCT frames and manually determine (measure) the available pullback length from the target area to the distal end of the guide catheter. A flush volume calculator, or lookup table with predefined flush volumes, can be provided as part of the software (in program form), on in an instruction-for-use (IFU) sheet for each given catheter, or in an interactive graphical user interface (GUI), or any other manner known to persons skilled in the art. Then, the user can refer to the measured pullback length and provided formula to calculate and set the actual pullback and flush settings. This embodiment can be implemented on any existing OCT system with a significant improvement.

In another embodiment, the guide catheter is preferably identified using specifically designed software algorithms which can be applied to any catheter regardless of manufacturer or imaging modality. In this case, a first OCT pullback is performed without contrast injection and the OCT data is displayed in a standard view of a display device of the system. The user may let the system know this is a range finder pullback, so that no contrast is injected and the system is adjusted to (at least temporary) record blood field images. The software algorithm may prompt the user to respond as to whether the guide catheter is present in at least one frame of the pullback images. To this end, the software may prompt the user to scroll through the set of images (non-flush pullback images) to the first frame where the guide catheter appears. Otherwise, the user may identify the location of the guide catheter in the non-flush pullback images in any other manner. Once the guide catheter has been identified by the user, the software algorithm takes over and does the pullback length and contrast volume calculations. The system software may then prompt the user to choose whether to accept the calculated settings or use conventional protocol setting. To this end, the system may cause the calculated pullback length and contrast volume be displayed for the user to make a decision. If the user accepts the calculated parameter, a second OCT pullback is performed with contrast injection only within the range of the calculated pullback length and using the calculated contrast volume.

In a further embodiment, specific software algorithms are added to the system for automatic detecting the guide catheter in the OCT images, calculating the necessary pullback length, and calculating the contrast volume as function of the pullback length. To this end, a first OCT pullback is performed without contrast injection, and the first pullback may or may not be displayed. The non-flush pullback images are processed with a guide catheter detection algorithm which automatically detects the guide catheter if present in at lease one frame of the OCT data. In this case, the system is preferably programed to determine the first frame where guide catheter is present. Then, the system automatically measures the available pullback length, and calculates the contrast volume for the pullback length. In this case too, the software algorithm may then prompt the user to accept the calculated settings, modify the calculated settings, or chose conventional protocol settings to perform a second OCT pullback with contrast injection.

FIG. 7 illustrates an exemplary flow process for controlling the OCT system to perform guide catheter tip detection and calculation of effective (necessary) pullback distance, as well as calculation of a reduced dose of contrast agent for flushing during OCT imaging. The process of FIG. 7 assumes an operational state in which a non-illustrated system console including computer 190 undergoes a system setup. System console setup may include, for example, executing a booting sequence of computer 190 and initializing the system software that operates the OCT system 100. In addition, system setup may include the computer 190 accessing executable software code stored in data storage memory 192 and initiating an imaging operation upon receiving a command prompt from a user of the system.

According to FIG. 7, at step S702 an imaging catheter is delivered to a target area 172 (or near a known reference 171) of a given lumen sample 170, preferably with image guidance (e.g., in a case of cardiovascular imaging, angiophrapy guidance can be used). This step S702 is considered to occur in a conventional or known manner, e.g., as part of a calibration process, such as the z-offset calibration. Since image guidance can be used at step S702, the location of the target area 172 with respect to the tip imaging probe 250 can be recognized and recorded at this step. In this manner, at step S702, the OCT system drives (translates) the imaging probe (catheter 160) into the lumen and positions the probe in the lumen such that the distal end of the imaging core (optical probe 250) is at a depth (or plane) necessary to irradiate the target area 172. The target area may refer to an intraluminal region desired to be examined for diagnosis or treatment. In cardiovascular imaging, the target area 172 may include anatomical structures or features, such as known or suspected pathological structures including regions with plaque, possible thrombus, calcifications, stenosis, areas of a vessel-wall thickening, necrotic regions along a vessel wall, and the like.

At step S704, the computer 190 of OCT system 100 automatically initiates a non-flush pullback process. The non-flush pullback process can be done as part of the calibration process (e.g., as part of the z-offset calibration at the beginning of an imaging operation). A non-flush pullback is a pullback operation executed without displacing the medium surrounding the distal end of the optical probe of catheter 160 (i.e., without blood displacement). In other words, the non-flush pullback is a pullback operation executed without injecting contrast agent into the lumen.

At step S706, the computer 190 collects and processes the OCT images obtained during the non-flush pullback. Here, it should be noted that while intravascular OCT imaging may be significantly impeded by the presence of blood, OCT imaging of the catheter and guide catheter is less affected by the presence of blood, and thus the system is able to assess the presence (and location) of the guide catheter even when imaging through blood. At step S706, processing of the OCT images of the blood field may include real time image analysis and displaying of a plurality of image frames, e.g., as those illustrated in FIGS. 5A through 5D. In this step, since the OCT images are used only for determining the presence and location of the guide catheter, the OCT data may not be stored, or only the OCT data with presence of the guide catheter may be selectively stored. In other words, storing the OCT data of the non-flush pullback is optional because it is only necessary to review the OCT images in which the guide catheter is detected.

That is, the OCT pullback is performed without contrast injection, and the images are processed and displayed at step S706. At step S708, the OCT system 100 automatically determines (or prompts the user to determine) whether the guide catheter is found in the non-flush pullback images. If the guide catheter is found in at least one of the non-flush pullback images, the flow proceeds to S710. If the system (or the user) determines that the guide catheter has not been found in the non-flush pullback images (NO at S708), the flow proceeds to step S730.

In general, when the OCT system is used to image a target area which is relatively near (proximal) to the catheter guide distal end, the non-flush pullback will most likely detect the catheter guide in one or more of the OCT image frames. However, when the imaging core of the OCT catheter is positioned to image a target area which is relatively far (distal) from the catheter guide distal end, it is likely that the non-flush pullback will not detect the guide catheter. Therefore, in the case where the OCT system does not detect the guide catheter in at least one of the image frames (NO at S708), the OCT system causes the imaging probe to perform the flush clearance and pullback operations under standard protocol.

If the guide catheter has been found (YES at S708), computer 190 may store only those images frames where the guide catheter is detected and may not store all other image frames where only the blood field is detected.

At step S710, the computer 190 can automatically select one or more frames of the OCT image data in which the distal end of the guide catheter is shown. For example, one of the frames shown in FIG. 5B or FIG. 5C can be automatically selected based on certain predetermined criteria or parameter. Here, for example, one or more of the following parameters can be used to determine if the distal end of the guide catheter is present in one or more frames of OCT data.

In a case in which at least part a ring of a predetermined diameter (e.g., the known diameter of the guide catheter+/−certain threshold) is detected by analyzing the intensity value of the one or more OCT image frames, it can be determined that the tip of guide catheter 270 is present. In a case in which at least part of a ring of a predetermined intensity value or more is detected in the one or more OCT image frames, and the intensity outside of the ring rapidly tapers off (the intensity outside of the ring represents only the un-cleared blood field), it can also be determined that the guide catheter 270 is present. Another parameter would be to look for the sudden change in brightness intensity when going from last blood-field frame to the first guide catheter frame (i.e., the frame where the guide catheter is first present).

Another guide catheter tip detection method may include detecting the sun-like ray pattern of the braided section of the guide catheter. In this case, as noted above, the braided section would be easiest to detect because it produces a distinct appearance like sun rays. Here, it possible to use the distal most braided frame (the first frame showing the braided section of the guide catheter, e.g., FIG. 5D) as an approximation of the location of guide catheter tip. To make the detection more accurate, it is possible to consider a predetermined (fixed) number of frames corresponding to the nominal soft tip length for guide catheters. For example, in FIGS. 5A-5D, Frame 2 (FIG. 5B) corresponds to the first frame in which the guide catheter tip appears, and Frame 10 (FIG. 5D) corresponds to the first frame where the braided section of the guide catheter appears. In this manner, once the first frame showing the braided section is detected, a predetermined number of frames (e.g., 7 frames: Frame 3-9) is factored into the calculation process to more accurately find the location of the distal end of the guide catheter.

Moreover, it is possible to estimate the location of the distal end of the guide catheter by detecting a change in brightness between the braided section and the tip of the guide catheter. To that end, during the non-flush pullback, one could first look for the brightness level of the blood field, then at the soft tip of the catheter guide, and at distal end of the braided section, by looking for a change in brightness (such as a sudden change in brightness) as the imaging core moves from the blood field into the guide catheter. FIG. 6B illustrates an exemplary graph of possible brightness levels as a function of the pullback direction, length, and/or time linear movement of the probe. For example, as shown in FIG. 6B, initially the OCT signal intensity is low because only the blood field is detected. As the pullback of the imaging catheter advances, the OCT signal intensity increases to a certain level when scattering from the guide catheter tip is detected. Finally, when the scattering from the guide catheter braided section is detected, the OCT signal intensity (the OCT data) reaches a maximum intensity level. Therefore, it is possible to also factor the change in brightness intensity of the OCT signal during a non-flush pullback to determine the location of the guide catheter distal tip.

Once the computer 190 detects one or more frames that includes the distal end of the guide catheter 270, at step S712, the computer 190 can calculate the actual (or effective) pullback length which is a distance from the target area 172 to the distal end of the guide catheter 270 (refer to FIG. 4A). To that end, for example, at step S712, the computer 190 can analyze the number of frames obtained in the non-flush pullback operation. Since each frame can be obtained at a predetermined distance L depending of the scanning rate of the system (refer to FIG. 4A), an algorithm can be programed in computer 190 to calculate the distance between the target area 172 and the distal end (tip) of the guide catheter 270. This distance can be considered as the effective pullback distance which is necessary to safely scan the target area 172 and stop the flushing process and the pullback process before the optical probe enters the guide catheter. After the actual pullback distance has been calculated at step S712, the processing algorithm advances to step S714.

At step S714, the computer 190 calculates the volume of the contrast agent based on the calculated (actual) pullback length. In this step S714, the computer 190 can access information stored beforehand in its memory about the infusion speed and/or infusion rate for specific types of lumens being imaged. Once the actual pullback length is calculated, and infusion speed or infusion rate is known, the computer 190 can calculate an adjusted volume of contrast agent based on the calculated pullback length. For example, as noted above, standard flushing protocol for certain types of vessels calls for an infusing rate of 4.00 ml/s. In this case, the computer 190 can use the standard infusing rate and the actual pullback length to calculate the reduced contrast volume, as explained more in detail below.

At step S716, computer 190 stores the calculated parameters including the calculated reduced volume of contrast agent and the calculated effective pullback length. Once the calculated parameters have been stored, the flow process continues to step S718, where the process begins anew.

At step S178, the computer 190 displays the pullback and flush parameters according to the values stored in memory at step S716. At step S718, the user is prompted to accept or reject the calculated pullback and flush parameters. If the user accepts, the parameters (YES at S718), the flow process advances to step S720. If the user does not accept the calculated parameters (NO at S720), the OCT system 100 transitions to step S730.

At step S720, the computer 190 initiates a flush pullback process only within the range of the calculated pullback length, and using the reduced contrast volume. Specifically, at S720, the system triggers a media clearance process (contrast flushing) according to the calculated volume of contrast agent. Here, the infusion rate and/or pullback speed may be adjusted according to the calculated parameter. At step S722, the computer 190 triggers a pullback operation using the adjusted speed necessary to scan the calculated pullback length in a given amount of time. At step S724, the computer 190 also starts a recording mode process in which the computer acquires and records OCT data obtained from within the cleared range of the lumen. Optionally, the computer also displays the imaging results for observation of the user. It is noted that although steps S720, S722, and S724 are listed as separate events, these steps could be started substantially simultaneously, or some steps (e.g. pullback and recording) may be initiated a very brief moment after the contrast flushing starts. That is, the pullback and recording could be delayed with respect to the starting of the flush clearance until a clear image of the lumen can be recorded. The specific details of timing, moving speed, contrast volume injection rate, etc., necessary to perform the flush pullback can be adjusted according to specific circumstances, after the clearance range and reduced contrast volume have been calculated. Methods and apparatus of blood clearing technologies, such as those described in publication US 2014/0142427 A1 which is incorporated by reference in its entirety, can be improved by the novel techniques provided in the present disclosure.

In this embodiment software algorithms are added for detecting the guide catheter in the OCT images. An OCT pullback is performed without contrast injection and may or may not be displayed. The OCT images are processed with a guide catheter detection algorithm which automatically detects the guide catheter if present. The software algorithm preferably determines the first frame in which the guide catheter appears so that only the tip of the guide catheter is recognized. Various non-limiting ways of recognizing the tip of the guide catheter are proposed, but a person skilled in the art could modify, combine, or device new processes based on the present disclosure. Once the distal end of the guide catheter is recognized, the software algorithm automatically measures the available pullback length and calculates the contrast volume. The software may then prompt the user to accept the calculated settings, may prompt the user to repeat the non-flush pullback to confirm the calculations are accurate, and the software can set automatically the calculated parameters for the next pullback operation, or can display for the user to confirm.

According to one aspect of the present disclosure, a flush protocol as Function of Pullback Length and Speed can be used to calculate a reduced dose of contrast agent. The flush protocol used most commonly with OCT imaging is 14 ml flush volume injected at 4 ml/s with a power injector or with a manual syringe. This 3.5-second-long flush is typically used to provide clearing for a 2-second-long OCT pullback which allows for 1.5 seconds delay for clearing to develop and for the pullback to be triggered manually by the user or through automatic detection of the clearing state, by a software algorithm. The initial "delay time" needed for clearing and triggering is independent of the subsequent "imaging time". The delay time depends on the vessel native flow rate and the processing and reaction time of the user or the clearance detection algorithm.

The flush protocol can be modeled with simple equations, as follows:

$$\text{Pullback Time} = \text{Pullback Length}/\text{Pullback Speed} \quad (1)$$

$$\text{Flush Time} = \text{Pullback Time} + \text{Delay Time} = \text{Pullback Time} + 1.5 \text{ s} \quad (2)$$

$$\text{Flush Volume} = \text{Infusion Rate} * \text{Flush Time} = 4 \text{ ml/s} * \text{Flush Time} \quad (3)$$

$$\text{Flush Volume} = 6 \text{ ml} + 4 * \text{Pullback Length}/\text{Pullback Speed} \quad (4)$$

For a Pullback Speed of 40 mm/s, the flush volume is as follows:

$$\text{Flush Volume} = 6 \text{ ml} + \text{Pullback Length}/10 \quad (5)$$

Table 1 below summarizes a few examples of possible contrast dose reduction according to the present disclosure

TABLE 1

| Flush Volume Table for Pullback Speed = 40 mm/s at different pullback lengths | | | | |
|---|---|---|---|---|
| Pullback Length (mm) | Imaging Time (sec) | Flush Volume (ml) | Flush Time (sec) | Contrast volume saving |
| 80 | 2.0 | 14 | 3.5 | 0 ml |
| 60 | 1.5 | 12 | 3.0 | 2 ml |
| 40 | 1.0 | 10 | 2.5 | 4 ml |
| 20 | 0.5 | 8 | 2.0 | 6 ml |

Using the Table 1 above, it is seen that contrast dose volume can be reduced by up to 50% for pullbacks where the target area is near the distal end of the guide catheter.

The calculation of the flush volume is not limited to the above equations (1)-(5); any known or newly devised formulas may be applicable. For example, the flush volume calculation from the Gutierrez-Chico paper or other custom equation(s) for flush volume as a function of limited-range pullback length could be used. As an example, the vessel-dependent infusion rate from Gutierrez-Chico in equation (3) above could be used.

The above embodiment can be modified to give the user more personalized control. In an alternative embodiment, the guide catheter can be manually identified by the OCT user from the non-flush pullback, and software tools are added only for automatically calculating optimal pullback range and flush parameters. In this case, first an OCT pullback is performed without contrast injection, and the OCT images are displayed in a standard view as any other pullback would be. The user of the system is trained or prompted to find the guide catheter by visually analyzing the OCT images. To this end, the user may let the software know that the initial pullback is a range finder pullback. In this case, after the initial non-flush pullback, the software may prompt the user to respond whether the guide catheter is present in the OCT images. The software may prompt the user to scroll to the first guide catheter frame or to otherwise identify the location of the guide catheter in one or more frames the pullback images. Once the guide catheter has been identified by the user, the software takes over and executes the pullback length and contrast volume calculations. The software may then prompt the user to accept the calculated settings which can then be set automatically or displayed for the user to set manually.

In a further alternate embodiment, it is envisaged that the pullback length can be calculated based on a reference other than the location of the guide catheter. Patients who have undergone coronary artery bypass surgery and need follow-up exams or develop in-stent restenosis (ISR) are often referred for percutaneous coronary intervention. Specifically, for patients with stents, coronary artery Computed Tomography Angiography (coronary CTA) is generally used to detect the borders of the stent, but is deficient in assessing the actual state of the stent lumen such as calcification which causes narrowing (stenosis) of the operated vein. In-stent restenosis occurs at a relatively high rate, and patients with prior stent placement comprise a good proportion of patients referred for invasive coronary angiography. In these cases, the pullback length and optimal contrast volume could be based on the detection of the stent itself within the lumen.

Figure 8:
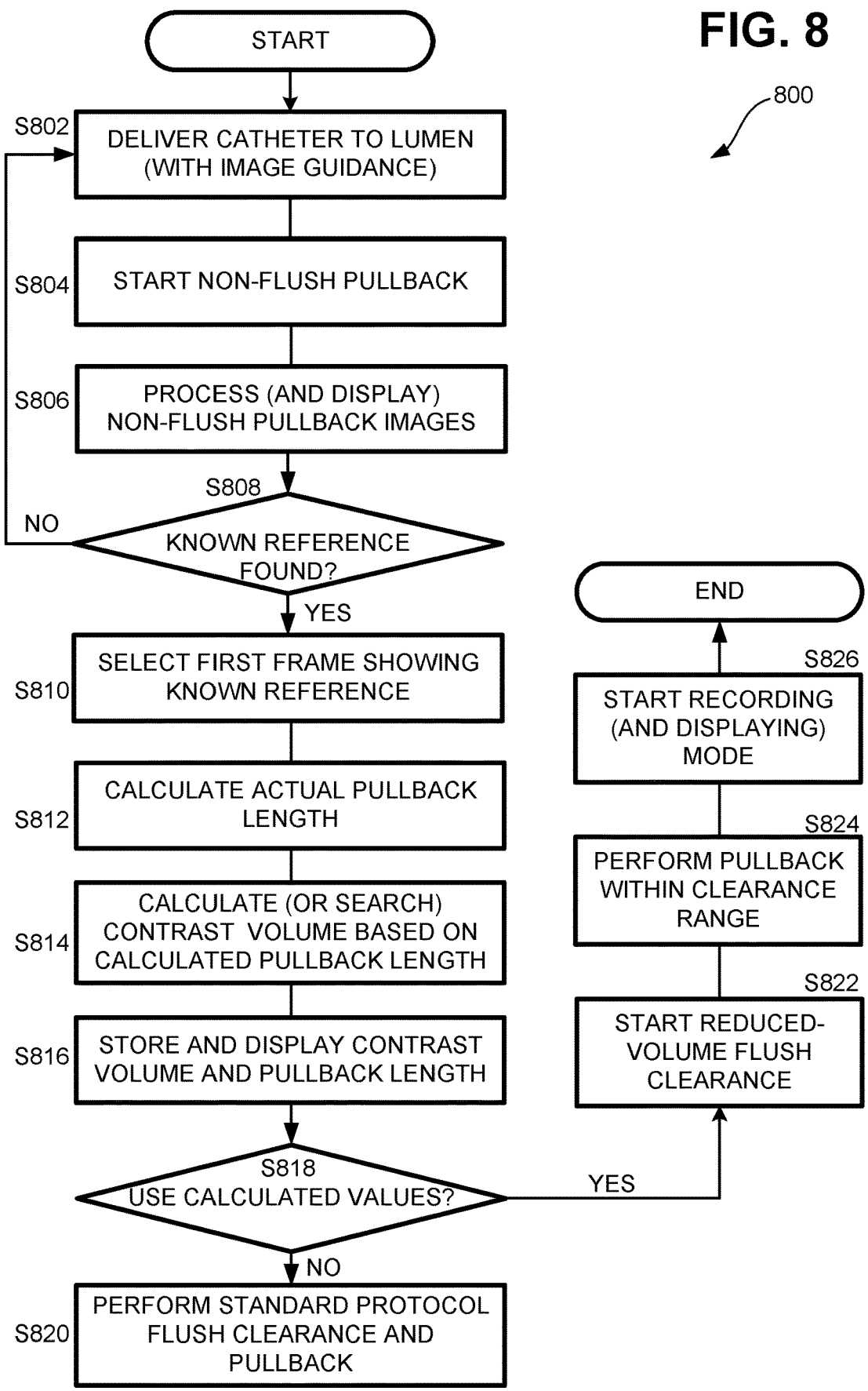
FIG. 8 illustrates a second exemplary range finding algorithm for controlling the OCT system 100 to perform luminal clearance according to a second embodiment.

FIG. 8 illustrates an alternative exemplary flow process for controlling the OCT system to perform calculation of an effective (necessary) pullback distance, as well as calculation of a reduced dose of contrast agent, based on a known reference within the lumen itself rather than looking for the guide catheter tip. The process of FIG. 8 is similar to that of FIG. 7 in that it assumes an operational state in which the computer 190 undergoes a system setup. System setup may include, for example, executing a booting sequence of computer 190 and initializing the system software that operates the OCT system 100. In addition, system setup may include, the computer 190 accessing executable software code stored in data storage memory 192 and initiating an imaging operation upon receiving a command prompt from a user of the system.

In the flow process of FIG. 8, at step S802, the system (or user) delivers the catheter 160 to a target area of interest (e.g. a stented area) inside a patient's lumen (e.g., a coronary artery) using image guidance, such as fluoroscopy or coronary CTA. At step S704, the OCT system 100, under a user's command, initiates a non-flush pullback. That is, the OCT pullback is performed without contrast injection, and the images are processed and displayed at step S806. At step S808, the OCT system 100 automatically determines (or prompts the user to determine) whether a known reference 171 of the lumen itself is found in the non-flush pullback images. As noted above, the known reference could be the stent within an artery of a patient. If the known reference is found in at least one of the non-flush pullback images, the flow proceeds to S810. If the system (or the user) determines that the known reference has not been found in the non-flush pullback images (NO at S808), the system or user may reposition the catheter within the lumen so that the imaging core of the probe is located at a depth appropriate for imaging the target area. In this case, the non-flush pullback can be repeated a predetermined number of times without wasting contrast or exposing the patient to any contrast agent until the target area and/or a known reference are found in the non-flush pullback images.

Here, the criteria or parameter for detecting the known reference can be similar to that for detecting the guide catheter. In particular, the approximate location of a known reference such as a stent within the artery of a patient can be estimated before hand from a guidance modality such as coronary CTA. However, to more accurately detect the location of the stent edges, the computer 190 can use a process similar to that described with reference to FIG. 6B, whereby a change in brightness intensity levels can allow detection of the exact location of the stent edges along the lumen. That is, when the known reference is a stent within an artery of a patient, a change in brightness intensity of in the one or more OCT image frames which corresponds to a change in the intensity of light reflected from the blood field to the intensity of light reflected from the stent can be indicative of the location of the known reference. When the known reference is found (YES in S808), the process continues to step S810.

At S810, the software (or the user) selects a first frame out of the non-flush pullback images showing the known reference. Once the location of the known reference has been found, at step S812, the computer 190 can calculate the actual (or effective) pullback length which could be the distance from a target area (e.g. the area distal to the stent) to the known reference (e.g., an edge of the stent). Or the actual (or effective) pullback length could be the distance arbitrarily chosen from the known reference (e.g., an arbitrary distance from the proximal or distal edge of the stent). This process is similar to finding the distal end of the guide catheter as shown in FIG. 4A, and then calculating a pullback distance. This pullback length is considered to be a clearance range sufficient to obtain accurate imaging of the target area and the inside of the stent without exposing the patient to excessive amounts of contrast agent.

Specifically, at step S812, the computer 190 can analyze the number of frames obtained along the non-flush pullback operation. Since each frame can be obtained at a predetermined distance L depending of the scanning rate, an algorithm can be programed in computer 190 to calculate the distance between, for example, the proximal and distal ends of the stent; this distance can be considered as the effective pullback distance necessary to safely scan the inside of the stent. At step S814, the computer 190 calculates the volume of the contrast agent based on the actual pullback length and, for example, the diameter of the lumen. To that end, the computer 190 can access information stored beforehand in its memory about the contrast volume necessary for specific types of lumens being imaged, and then calculate an adjusted contrast volume based on the calculated pullback distance. Alternatively, in the case of imaging a stented region of an artery, the diameter of the stent can be known beforehand by the OCT user.

At step S816, computer 190 can store the calculated parameters including the calculated volume of contrast agent and the calculated effective pullback length. At step S818, the computer 190 may prompt the user to make a decision as to whether to use the calculated values or not. In the case that the user accepts to use (YES in S818) the calculated effective pullback distance and the adjusted contrast volume, the flow proceeds to S822. In the case where the user does not accept to use the calculated pullback distance and adjusted contrast volume (NO in S818), the flow proceeds to S820. At step S820, the user can command the system to perform the flush clearance and pullback operation according to standard protocols in a known manner.

At step S822, the computer 190 initiates a flush clearance process using the reduced volume stored at S816. At step S824, the computer 190 initiates a pullback operation. At step S826, the computer 190 may also initiate recording and displaying of the OCT imaging data. Here, steps S822-S826 are similar to steps S720-S724, as already described above.

The above-described algorithms can be used with any OCT system including those that are commercially available single modality systems. Although, the non-flush pullback operation may add a few seconds to the overall imaging procedure, the optimization of the flush pullback operation can offset that added time. However, even if few seconds are added to the imaging procedure, the reduction in use of contrast agent and minimization of patient exposure to potential side effects of contrast agent are well worth the few seconds of added time to the imaging procedure.

The range finding algorithms disclosed above allow for an optimized flush and pullback plan to be established beforehand which makes it possible to minimize contrast dose while avoiding premature or delayed stops of contrast infusion and pullback movement. A main drawback of previously known flush and pullback techniques has been the delay time. OCT can be performed at up to 40 mm/s with an entire pullback procedure being performed in about 2 seconds or even less. Delays in processing the OCT image, detecting the guide, and conveying a stop signal reduce the effectiveness of any potential gains from early stopping. Further, any errors in inaccurate processing algorithms could cause a premature stop which could ruin an otherwise good pullback and necessitate an additional pullback and additional contrast injection. The embodiments described herein allows an optimized flush and pullback plan to be established beforehand which makes it possible to minimize contrast dose while avoiding premature stops.

The algorithms and processes disclosed herein improve the calculation of optimal flush volume based on a segment of interest (SOI) length determined from an angiogram. Specifically, because angiography guidance is a projection based imaging modality, it suffers from foreshortening which adds uncertainty to any vessel length measurement. The present disclosure can provide a significantly more accurate measurement of the vessel segment of interest length through the use of OCT imaging in the non-flush pullback operation. Further the flush volume calculation presented in the present disclosure is a more accurate representation of the actual model of clearing. To demonstrate this, consider a case where SOI was only 1 mm. Assuming a 40 mm/s pullback rate, the imaging time is only 0.025 s. Assuming a 4 ml/s infusion rate, the Gutierrez equation calculates a flush volume of 2×4 ml/s×1 mm÷40 mm/s=0.2 ml which will not produce clearing at all, let alone provide an adequate window to trigger. For the same example of a 1 mm SOI, the present disclosure provides an equation (Equation 5) which calculates the adjusted flush volume as follows: 6 ml+1 mm+10 mm/ml=6.1 ml. This result will provide an adequate window to clearing and pullback trigger. The equation (Equation 5) of the present disclosure also produces lower contrast doses for longer pullbacks. Consider a commercially available high resolution pullback of 54 mm at 18 mm/s. The imaging time is 3 seconds. Assuming a 4 ml/s infusion rate, the Gutierrez equation calculates a flush volume of 2×4 ml/s×54 mm÷18 mm/s=24 ml. In contrast, the present disclosure uses the algorithm with Equation 5, which calculates a flush volume of 6 ml+4 ml/s*54 mm+18 mm/s=18 ml. Therefore, at both the high and low end of pullback time the present disclosure provides clearance ranging algorithms which produce a preferable flush protocol.

According to the present disclosure, various advantages can be obtained with respect to known techniques that do not use OCT range finding for luminal clearance. For example, the novel techniques disclosed above applies to normal, single mode OCT imaging modalities and to multi-modality imaging with OCT. Indeed, a notable advantage of the present disclosure is that a catheter with second modality is not required; the novel luminal ranging algorithms can be implanted on standard commercially available OCT only systems. The first pullback with no contrast injection serves to inform and optimize the second (flush) pullback with adjusted contrast volume and optimized pullback length. The ranging algorithms can be modified to include automatic or manual detection of the guide catheter frame in the non-flush pullback. The determination of the actual length is fast, and provides data with accurate location of the guide catheter in the vessel.

The disclosed algorithms include a formula for recommended reduced contrast flush settings as a function of the pullback length, but the formula can be modified depending on parameters of specific applications. The recommended contrast settings are easy to apply and allow the user to evaluate the amount of contrast reduction before starting the second (flush) pullback operation. Experimental results showed that the proposed techniques disclosed herein can reduce contrast dose by up to 50% for proximal pullbacks without affecting the quality of imaging. Decreasing the dose of potentially harmful contrast material makes OCT procedures safer and more attractive. Furthermore, experimental results have shown that the disclosed technique can reduce OCT file size and post-acquisition image processing time because OCT data recording can be more precisely controlled to occur only within the calculated range of intraluminal clearance.

Certain aspects of the present disclosure can be realized by the computer 190 of the OCT system 100 or similar apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like. An I/O interface can be used to provide communication interfaces to input and output devices, which may include a keyboard, a display, a mouse, a touch screen, touchless interface (e.g., a gesture recognition device) a printing device, a light pen, an optical storage device, a scanner, a microphone, a camera, a drive, communication cable and a network (either wired or wireless).

The detector interface also provides communication interfaces to input and output devices. The detector may include, for example a photomultiplier tube (PMT), a photodiode, an avalanche photodiode detector (APD), a charge-coupled device (CCD), multi-pixel photon counters (MPPC), or other. Also, the function of detector may be realized by computer executable instructions (e.g., one or more programs) recorded on a Storage/RAM.

In referring to the description, specific details are set forth in order to provide a thorough understanding of the examples disclosed. In other instances, well-known methods, procedures, components and circuits have not been described in detail as not to unnecessarily lengthen the disclosure. Unless defined otherwise herein, all technical and scientific terms used herein have the same meaning as commonly understood by a person of ordinary skill in the art to which this disclosure belongs. However, the disclosure of this patent specification is not intended to be limited to the specific terminology so selected and it is to be understood that each specific element includes all technical equivalents that operate in a similar manner.

The term "about" or "approximately" as used herein means, for example, within 10%, within 5%, or less. In some embodiments, the term "about" may mean within measurement error. In this regard, where described or claimed, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range, if recited herein, is intended to include all sub-ranges subsumed therein.

The terms first, second, third, etc. may be used herein to describe various steps, elements, components, regions, parts and/or sections. It should be understood that these steps, elements, components, regions, parts and/or sections should not be limited by these terms or other thereof. These terms have been used only to distinguish one step, element, component, region, part, or section from another region, part, or section. Thus, a first step, element, component, region, part, or section discussed above and claimed below could be termed a second element, component, region, part, or section without departing from the teachings herein.

The terminology used herein is for the purpose of describing particular embodiments only and is not intended to be limiting. As used herein, the singular forms "a", "an", "said" and "the", are intended to include the plural forms as well, unless the context clearly indicates otherwise. It should be further understood that the terms "includes" and/or "including", when used in the present specification, specify the presence of stated features, integers, steps, operations, elements, and/or components, but do not preclude the presence or addition of one or more other features, integers, steps, operations, elements, components, and/or groups thereof not explicitly stated. It is further noted that some claims may be drafted to exclude any optional element; such claims may use exclusive terminology as "solely," "only" and the like in connection with the recitation of claim elements, or it may use of a "negative" limitation.

While the present disclosure has been described with reference to exemplary embodiments, it is to be understood that the present disclosure is not limited to the disclosed exemplary embodiments. The scope of the following claims is to be accorded the broadest interpretation so as to encompass all such modifications and equivalent structures and functions.

What is claimed is:

1. A method for finding a range of lumen clearance for an optical coherence tomographic (OCT) imaging probe, wherein the probe has proximal and distal ends and includes an imaging core and a guiding conduit arranged concentrically to a probe axis, the method comprising:
   acquiring a first set of images of an inside of the lumen using the probe to irradiate the inside of the lumen, the first set of images being acquired while the imaging core of the probe irradiates a target area and is pulled back from a starting position towards the guiding conduit during a non-flush pullback operation;
   analyzing the first set of images to determine a location of the guiding conduit or a known reference within the lumen;
   calculating a range of lumen clearance based on the location, wherein the calculating of the range includes calculating, using the location, a pullback length which is a distance from the starting position to a distal end of the guiding conduit;
   calculating a volume of contrast agent to be injected into the lumen, wherein the calculating of the volume is based on the calculated pullback length; and
   acquiring a second set of images of the inside of the lumen using the probe to irradiate the inside of the lumen only within the range of lumen clearance, the second set of images being acquired while the imaging core of the probe irradiates the target area and is pulled back towards the guiding conduit during a flush pullback operation.

2. The method according to claim 1,
   wherein performing the non-flush pullback operation includes translating the imaging core of the probe from the starting position in a direction from the distal end to the proximal end without injecting into the lumen any amount of contrast agent, and
   wherein performing the flush pullback operation includes injecting into the lumen the calculated volume of contrast agent into the lumen and translating the imaging core of the probe from the starting position in the direction from the distal end to the proximal end within the calculated range of lumen clearance.

3. The method according to claim 1, further comprising:
   calculating one or more of a pullback time, a pullback speed, a flush time, and/or an infusion rate for the flush pullback operation based on the calculated pullback length and the calculated volume of contrast agent.

4. The method according to claim 1,
   wherein acquiring the second set of images of the inside of the lumen within the range of lumen clearance includes acquiring a plurality of frames of OCT data in a distance from the starting position to the distal end of the guiding conduit or to the known reference.

5. The method according to claim 1,
   wherein acquiring the first set of images includes acquiring a plurality of frames of OCT data of the inside of the lumen, and
   wherein analyzing the first set of images includes identifying the distal end of the guiding conduit or the known reference in at least one frame of the frames of OCT data.

6. The method according to claim 1,
wherein analyzing the first set of images includes determining whether the guiding conduit or the known reference is present in at least one image of the first set of images acquired during the non-flush pullback operation.

7. The method according to claim 1, further comprising:
analyzing the first set of images to determine a parameter indicative of the presence of the guiding conduit, wherein the analyzing includes detecting presence of one or more of:
at least part of a ring of a predetermined diameter in one or more OCT image frames of the first set of images,
at least part of a ring of a predetermined brightness intensity value in one or more OCT image frames of the first set of images, and/or
a change in brightness intensity value corresponding to a change in light reflected from a blood field to light reflected from the guiding conduit in one or more OCT image frames of the first set of images.

8. The method according to claim 1,
wherein the known reference includes a stent and the lumen includes an artery of a patient, and
wherein a parameter indicative of the location of the known reference includes a change in brightness intensity which corresponds to a change in the intensity from light reflected by a blood field to the intensity of light reflected by the stent in one or more image frames of the first set of images.

9. The method according to claim 1, further comprising:
positioning the probe in the lumen using image guidance such that the distal end of the imaging core is positioned to irradiate the target area or the known reference.

10. A non-transitory computer-readable storage medium storing thereon computer executable code, which when executed by a processor, causes a computer to perform a method according to claim 1.

11. An apparatus configured to control lumen clearance in a pullback operation of an optical coherence tomographic (OCT) probe, the probe having proximal and distal ends and including an imaging core and a guiding conduit arranged concentrically to a probe axis, the apparatus comprising:
an electronic memory storing executable instructions; and
a processor in communication with the memory,
wherein the processor is configured to execute the instructions to:
acquire a first set of images of an inside of the lumen using the probe irradiate the inside of the lumen, the first set of images being acquired while the imaging core of the probe irradiates a target area and is pulled back towards the guiding conduit during a non-flush pullback operation;
analyze the first set of images to determine a location of the guiding conduit with respect to the target area;
calculate a range of lumen clearance based on the location of the guiding conduit, wherein the calculating of the range includes calculating, using the location, a pullback length which is a distance from a starting position to a distal end of the guiding conduit;
calculating a volume of contrast agent to be injected into the lumen, the calculating being based on the calculated pullback length; and
acquire a second set of images of the inside of the lumen using the probe to irradiate the inside of the lumen only within the range of lumen clearance, the second set of images being acquired while the imaging core of the probe irradiates the target area and is pulled back towards the guiding conduit during a flush pullback operation,
wherein the processor calculates the range of lumen clearance as a distance from the target area to the distal end of the guiding conduit, and sets the range of lumen clearance as a pullback length for the flush pullback operation.

12. The apparatus according to claim 11,
wherein the processor is further configured to:
trigger injection of the volume of contrast agent during the flush pullback operation.

13. An optical coherence tomography (OCT) system, comprising:
an imaging catheter comprising a guide catheter and a rotatable imaging core located within the guide catheter; and
a control system configured to control the imaging catheter to:
guide the imaging core through the guide catheter to an imaging start position inside a lumen;
acquire a first set of images inside the lumen while performing a non-flush pullback operation with the imaging catheter;
analyze the first set of images to determine a location of the guide catheter within the lumen;
calculate a range of lumen clearance based on the presence and/or location of the guide catheter, wherein the calculating of the range including calculating, using the location, a pullback length which is a distance from the imaging start position to a distal end of the guiding conduit;
calculating a volume of contrast agent to be injected into the lumen, the calculating being based on the calculated pullback length; and
acquire a second set of images of the inside of the lumen while performing a flush pullback operation with the imaging catheter.

14. The OCT system according to claim 13, wherein the second set of images is acquired controlling the imaging catheter to image the inside of the lumen only within the calculated range of lumen clearance.

15. The OCT system according to claim 14,
wherein the control system determines the location of the guide catheter based on one or more of:
detecting at least part of a ring of a predetermined diameter by analyzing a brightness intensity value of one or more OCT image frames in the first set of images,
detecting at least part of a ring having a predetermined brightness intensity value in one or more OCT image frames in the first set of images, and
detecting a change in brightness intensity values, which corresponds to a change in the intensity of light reflected from a blood field to the intensity of light reflected from the guide catheter, by analyzing one or more OCT image frames of the first set of images.

16. The OCT system according to claim 13, wherein the first set of images includes a plurality of OCT image frames.

17. The OCT system according to claim 13,
wherein the control system is further configured to calculate one or more of a pullback time, a pullback speed, a flush time, and/or an infusion rate for the flush pullback operation based on the calculated pullback distance and the calculated volume of contrast agent.

18. A method for finding a range of lumen clearance for an optical coherence tomographic (OCT) imaging probe, wherein the probe has proximal and distal ends and includes an imaging core and a guiding conduit arranged concentrically to a probe axis, the method comprising:
- acquiring a first set of images using the probe to irradiate the inside of the lumen, the first set of images being acquired while the imaging core of the probe irradiates a target area and is pulled back from a starting position towards the guiding conduit during a non-flush pullback operation;
- analyzing the first set of images to determine a parameter indicative of a presence of at least one of the guiding conduit or a known reference within the lumen;
- calculating a range of lumen clearance based on the parameter, wherein the calculating of the range includes calculating, using the parameter, a pullback length which is a distance from the starting position to a distal end of the guiding conduit;
- calculating a volume of contrast agent to be injected into the lumen, the calculating being based on the calculated pullback length; and
- acquiring a second set of images using the probe to irradiate the inside of the lumen,
- wherein the second set of images is acquired within the range of lumen clearance, and
- wherein the second set of images is acquired while the imaging core of the probe is pulled back towards the guiding conduit during a flush pullback operation.

* * * * *